United States Patent
Ning et al.

(10) Patent No.: US 7,933,079 B2
(45) Date of Patent: Apr. 26, 2011

(54) OPTICAL ASSEMBLY FOR MEDICAL IMAGING DEVICES

(75) Inventors: Alexander Ning, San Marcos, CA (US);
Robert Lu, Shanghai (CN); William Lucas Churchill, Bolton, MA (US);
Sergey S. Grigoryants, Malden, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 11/801,332

(22) Filed: May 8, 2007
(Under 37 CFR 1.47)

(65) Prior Publication Data

US 2008/0225410 A1    Sep. 18, 2008

Related U.S. Application Data

(60) Provisional application No. 60/798,492, filed on May 8, 2006.

(51) Int. Cl.
*G02B 7/02* (2006.01)
(52) U.S. Cl. ........................ 359/811; 359/808
(58) Field of Classification Search ................. 359/715, 359/754, 771, 781, 782, 808, 811, 716; 600/175, 600/176
See application file for complete search history.

(56) References Cited

U.S. PATENT DOCUMENTS

| | | | |
|---|---|---|---|
| 4,332,442 A | 6/1982 | Ookawa | |
| 5,087,989 A | 2/1992 | Igarashi | |
| 6,282,033 B1 | 8/2001 | Ning | |
| 6,398,723 B1 * | 6/2002 | Kehr et al. | 600/160 |
| 6,441,971 B2 | 8/2002 | Ning | |
| 6,654,187 B2 | 11/2003 | Ning | |
| 6,836,382 B2 | 12/2004 | Ning | |
| 6,856,465 B2 | 2/2005 | Ning | |
| 6,862,144 B1 | 3/2005 | Aguero | |
| 6,905,462 B1 | 6/2005 | Homma et al. | |
| RE38,799 E | 9/2005 | Ning | |
| 6,950,248 B2 * | 9/2005 | Rudischhauser et al. | 359/811 |
| 7,023,628 B1 | 4/2006 | Ning | |
| 7,173,774 B2 | 2/2007 | Ning | |
| 7,385,772 B2 * | 6/2008 | Forkey et al. | 359/819 |

(Continued)

FOREIGN PATENT DOCUMENTS

CH        538703 A1    6/1973

(Continued)

OTHER PUBLICATIONS

Written Opinion of the International Searching Authority prepared for International Application PCT/US2007/011232, European Patent Office, Aug. 11, 2008.*

(Continued)

*Primary Examiner* — David N Spector
(74) *Attorney, Agent, or Firm* — Finnegan, Henderson, Farabow, Garrett & Dunner, LLP

(57) ABSTRACT

Optical assemblies for use in medical or other devices so as to image an object under examination onto an image sensor include a plurality of lens elements that can be retained in lens barrel. The lens elements and the lens barrel can be sealed with a compressible gasket. In one example, at least one lens element is made of an injection-moldable plastic and at least one lens element is made of a relatively dispersive optical glass. A lens barrel diameter or lens diameter can be selected to permit access to the object under examination with surgical or other tools. Aperture plates can be situated so as to reduce flare in the object image.

7 Claims, 5 Drawing Sheets

U.S. PATENT DOCUMENTS

| | | | |
|---|---|---|---|
| 7,530,945 B2 * | 5/2009 | Rudischhauser et al. | 600/128 |
| 2002/0186478 A1 | 12/2002 | Watanabe | |
| 2004/0095499 A1 | 5/2004 | Ning | |
| 2004/0165090 A1 | 8/2004 | Ning | |
| 2005/0013018 A1 | 1/2005 | Ning | |
| 2005/0131279 A1 * | 6/2005 | Boulais et al. | 600/141 |
| 2005/0245789 A1 * | 11/2005 | Smith et al. | 600/159 |
| 2006/0193063 A1 | 8/2006 | Xu | |
| 2007/0249907 A1 | 10/2007 | Boulais et al. | |
| 2008/0186478 A1 | 8/2008 | Moroni et al. | |
| 2009/0219631 A1 | 9/2009 | Ning | |

FOREIGN PATENT DOCUMENTS

| | | |
|---|---|---|
| CN | 1373858 A | 10/2002 |
| DE | 102004049871 A1 | 4/2006 |
| JP | 05264895 A | 10/1993 |
| JP | 2004295119 A | 10/2004 |
| JP | 02090118 A | 6/2008 |

OTHER PUBLICATIONS

Letter from Alex Ning, PhD, to Kurt Lockwood dated Nov. 20, 2007, forwarded in e-mail to Melissa Szmigulski dated Nov. 20, 2007, 3 pages.

Letter from Alex Ning, PhD, to Kurt W. Lockwood dated Nov. 30, 2007, 1 page.

Written Opinion of the International Searching Authority and International Search Report prepared for corresponding International Application PCT/US2007/011232, European Patent Office, May 15, 2008.

* cited by examiner

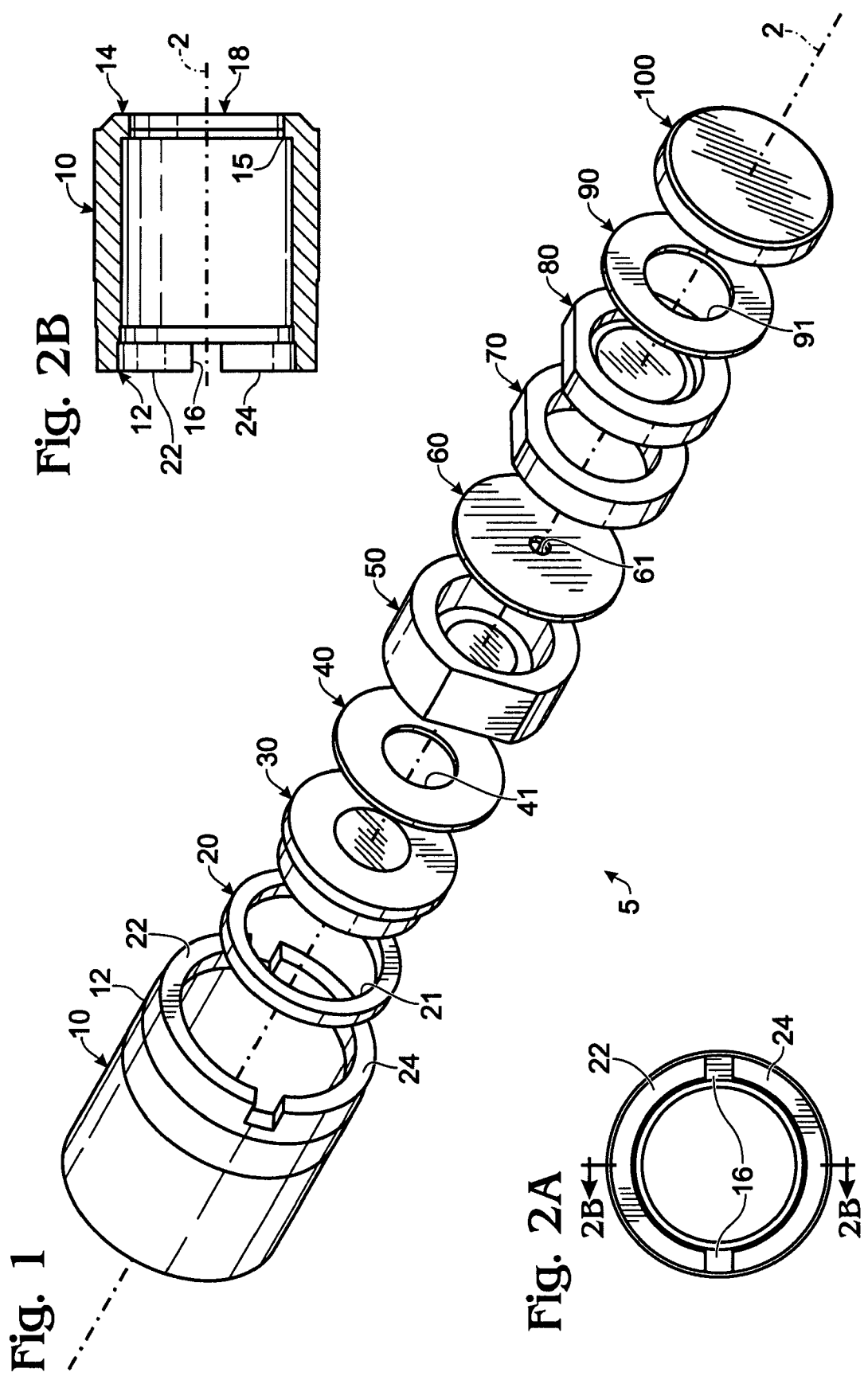

OPTICAL ASSEMBLY FOR MEDICAL IMAGING DEVICES

CROSS-REFERENCE TO RELATED APPLICATIONS

The present application claims the benefit of U.S. provisional application 60/798,492, filed May 8, 2006, that is incorporated herein by reference.

TECHNICAL FIELD

The present invention relates to medical devices in general and, in particular, to optical assemblies for medical imaging devices.

BACKGROUND OF THE INVENTION

As an alternative to performing more invasive procedures, many physicians are using minimally invasive devices to examine and/or treat internal body tissues of patients. Examples of such minimally invasive devices include endoscopes and catheters. Typically, such devices include an elongated shaft that is inserted into the patient and a mechanism for producing images from the distal end of the device. Such mechanisms include fiber optic imaging guides that transmit light to a proximally located camera. Alternatively, the devices may include an image sensor at the distal tip that produces electronic signals that are used to produce video images of the internal body cavity. To reduce the costs associated with repeated disinfection and repair of such devices, some endoscopes and catheters may be designed to be single-use. Examples of single-use endoscope designs are described in U.S. patent application Ser. Nos. 10/811,781, and 10/196,007, assigned to Boston Scientific Scimed, Inc., the assignee of the present application. These applications are herein incorporated by reference.

One factor that has limited the ability to make commercially feasible single-use endoscopes or imaging catheters is the cost of the required imaging optics. To make a practical single-use device, such optics should provide images that are as good as or better than those obtained with conventional re-usable devices. In addition, these optics should be inexpensive such that the cost of the overall device allows it to be used once and thrown away. Accordingly, improved optical assemblies, endoscopes, and medical imaging devices are needed.

SUMMARY

The present disclosure pertains to optical assemblies for use in medical devices such as endoscopes or imaging catheters. In one example, such an optical assembly includes a lens barrel having a number of stacked optical elements therein. The optical elements are compressed against an O-ring within the lens barrel to form an airtight seal in the lens barrel. In a representative example, the optical assembly includes a plurality of lens elements, and one or more of the lens elements are plastic, injection-molded lenses. These and other examples are described briefly in this summary so as to introduce a selection of concepts and features in a simplified form that are further described below in the Detailed Description. This summary is not intended to identify key features of the claimed subject matter, nor is it intended to limit the scope of the claimed subject matter.

According to representative examples, optical assemblies include a hollow lens barrel having an inner diameter, a distal opening, and a distal rim having an inner diameter that is less than the inner diameter of the lens barrel. A compressible gasket is situated within the lens barrel at the distal rim, and a lens is situated within the lens barrel and in contact with the compressible gasket such that the compressible gasket forms a seal between the distal rim of the lens barrel and the lens. In some examples, the compressible gasket is an O-ring. In additional examples, the lens is a multi-element lens and the lens barrel includes a proximal rim that is formed over a proximal-most optical element of the multi-element lens so as to urge the multi-element lens to at least partially compress the compressible gasket. In some examples, the seal formed by the compressible gasket can withstand a pressure of at least about 30 kP.

In additional representative examples, the multi-element lens includes at least a first lens situated at the distal rim of the lens barrel and having a negative optical power. The first lens is in contact with the compressible gasket so as to seal the lens barrel. In some examples, the first lens has a most object-wise surface that is a convex spherical surface and a most image-wise surface that is a concave aspheric surface. In other examples, the multi-element lens comprises, from most object-wise to most image-wise along a lens axis, a first lens, a second lens, a third lens, and a fourth lens. According to illustrative examples, the first, second, and third lenses are made of a common optical plastic, and the fourth lens is made of a flint glass. In other examples, the first through fourth lenses have optical surfaces defined by, from a most object-wise surface to a most image-wise surface:

| Surface | Radius of Curvature |
| --- | --- |
| 1 | +60.000 |
| 2 | +0.973 |
| 3 | −8.125 |
| 4 | −1.491 |
| 5 | +2.831 |
| 6 | −1.193 |
| 7 | −2.674 |
| 8 | infinite | wherein surfaces 2, 4, and 6 are aspheric surfaces further defined by respective conic constants and aspheric coefficients as follows:

| Surface | K | $a_2$ | $a_3$ | $a_4$ |
| --- | --- | --- | --- | --- |
| 2 | +0.5073543 | 0.0 | 0.0 | 0.0 |
| 4 | +0.0 | −0.018796213 | −0.036606083 | −0.068263035 |
| 6 | +0.0 | +0.11189657 | +0.014471055 | +0.044036317 | wherein K is a conic constant, and $a_2$, $a_3$, and $a_4$ are aspheric power series coefficients.

In representative examples, the second lens includes an object-wise concave optical surface and has a positive power. In additional examples, a first aperture plate and a second aperture plate are situated between the first lens and the second lens, and the third lens and the fourth lens, respectively. In further examples, an aperture stop is situated between the second lens and the third lens.

Multi-element lenses configured to form an image of an object at an image surface comprise, from object-wise to image-wise along an optical axis, a first, a second, and a third lens element of a common optical material, and a fourth lens element of a different lens material, wherein an aperture stop is situated between the second and third lenses. In some examples, the first lens and the fourth lens have negative optical power, and the second lens and the third lens have positive optical power. In further examples, most image-wise surfaces of the first lens, the second lens, and the third lens are aspheric, and are defined by

| K | $a_2$ | $a_3$ | $a_4$ |
|---|---|---|---|
| +0.5073543 | 0.0 | 0.0 | 0.0 |
| +0.0 | −0.018796213 | −0.036606083 | −0.068263035 |
| +0.0 | +0.11189657 | +0.014471055 | +0.044036317 | respectively, wherein K is a conic constant, and $a_2$, $a_3$, and $a_4$ are aspheric power series coefficients. In some examples, an aperture plate defining a flare reducing aperture is situated between the first lens and the second lens or the third lens and the fourth lens or both. In representative examples, the first lens and the fourth lens have negative optical power, and the second lens and the third lens have positive optical power. In additional examples, the fourth lens includes an object-wise concave surface. In still further examples, an aperture stop is situated between the second lens and the third lens.

These and other aspects of the disclosed technology will become more readily appreciated by reference to the following detailed description and the accompanying drawings.

BRIEF DESCRIPTION OF THE DRAWINGS

FIG. 1 is an exploded view of a representative optical assembly according to the disclosed technology.

FIGS. 2A-2B illustrate a lens barrel for use with the representative optical assembly of FIG. 1.

DETAILED DESCRIPTION

Figure 3A:
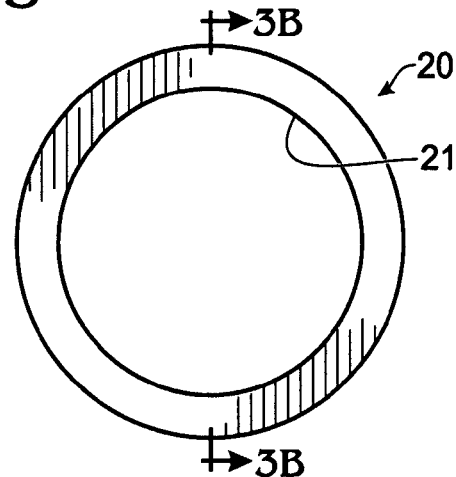
FIGS. 3A-3B illustrate an O-ring for use with the optical assembly of FIG. 1.

As used in this application and in the claims, the singular forms "a," "an," and "the" include the plural forms unless the context clearly dictates otherwise. Additionally, the term "includes" means "comprises." Further, the term "coupled" means electrically, mechanically, or optically coupled or linked and does not exclude the presence of intermediate elements between the coupled items.

The described systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

As used herein, "lens" refers to a single optical element having two refractive surfaces (i.e., a "singlet") or an assembly of two or more singlets, including optical elements that are secured to each other as in cemented doublets or otherwise fixed with respect to each other. Such combinations of lens elements can also be referred to as multi-element lenses. In the disclosed examples, dioptric lenses are provided having optical power based entirely on refractive optical elements. In other examples, reflective imaging optics or catadioptric optical elements can be provided. For convenience, light propagation from an object to an image can be illustrated with rays extending from left to right along an optical axis that extends through one or more lens elements. Typically, an optical axis extends through a geometric center of a lens and is perpendicular to a tangent plane to the lens at the lens center. The optical axis can be single straight line, or one or more line segments if fold mirrors or other reflective optical elements such as prisms are included. An optical axis can be considered as extending from an object (or object surface) to an image (or image surface). Directions along the optical axis can be referred to as object-wise (in the direction of the object) or image-wise (in the direction of the image). These directions are selected for convenient description as it will be appreciated that image and object locations can be interchanged depending on a particular application. For example, a lens assembly configured to produce an object to image demagnification of ½ can be reversed to, for example, produce an object to image magnification of 2.

Surface curvatures for reflecting and refracting optical surfaces can be described based on surface sag Z along an optical axis as a function of a perpendicular distance r from a selected surface point to the optical axis. Using one common representation, surface sag Z(r) can be expressed as:

$$Z(r) = \frac{Cr^2}{1 + \sqrt{1-(1+K)C^2r^2}} + a_1r^2 + a_2r^4 + a_3r^6 + a_4r^8 + a_5r^{10},$$

wherein C is a surface curvature (a reciprocal of the surface radius of curvature), K is a conic constant $K=-e^2$, wherein e is a surface eccentricity that is associated with a surface corresponding to a conic section, and $a_1, a_2, a_3, a_4$, and $a_5$ are aspheric power series coefficients. The value of a surface eccentricity e is greater than one for hyperboloids, equal to one for paraboloids, between zero and one for ellipsoids, and zero for spherical surfaces.

Lenses and lens elements are referred to as having a positive optical power if incident ray directions parallel to a lens optical axis tend to be directed toward the optical axis after refraction. Such lens elements can produce real images of an object. Negative optical powers are associated with lenses that tend to direct such parallel rays away from the lens axis and typically do not produce real images of an object without additional lens elements.

As indicated above, the disclosure pertains to optical assemblies for use in, for example, imaging medical devices such as endoscopes or catheters, other medical or non-medical imaging devices, and methods of imaging for medical as well as other applications. In some convenient examples, optical assemblies are sufficiently inexpensive to manufacture such that they can be incorporated into single-use medical devices. In other examples, optical assemblies can be configured for use in re-usable devices. Improved image contrast and lens transmission can be obtained in such assemblies by providing broadband or narrowband anti-reflective coatings on one or more lens surfaces. In one representative embodiment, an anti-reflective coating is present on all lens surfaces except those of a front-most (object-wise) lens element. Light controlling apertures for flare reduction and f/number selection are generally defined in aperture plates. Such plates can be formed of a variety of materials and are provided with suitable apertures, typically circular apertures configured to be centered on a lens optical axis.

As indicated above, one use of the optical assemblies disclosed herein is in single-use medical imaging devices such as endoscopes. In one embodiment, the optical assembly disclosed below is fitted into an image sensor insert that supports one or more LEDs and an image sensor as disclosed in U.S. patent application Ser. Nos. 10/811,781, and 10/956,007 both of which are incorporated herein by reference. Such endoscopes are also described in further detail below. However, other configurations of the optical assembly of the disclosed optical assemblies and an image sensor can be used.

Referring to FIG. 1, an optical assembly 5 includes a lens barrel 10 in which a number of lenses, aperture plates, spacers, and mounting plates as further described below are situated along an optical axis 2. As shown in FIG. 1 and FIG. 2B, the lens barrel 10 comprises a plastic barrel having a distal rim 14 that defines a lens barrel opening that is smaller than an inner diameter of the lens barrel 10 so as to form a lip 15 that is configured to retain optical and other elements in the lens barrel 10. A proximal rim 12 has one or more tabs or the like that can be formed over the last (most image-wise) optical or other element of the optical assembly 5 by heating, bending, molding, or similar technique in order to secure a stack of optical elements including spacers and aperture plates in the lens barrel 10 at the proximal rim 12. In a typical application, the distal rim 14 is object-wise of the proximal rim 12 so that optical radiation from an object under investigation is received by the optical assembly 5 at the distal rim 14 and directed to an image plane or other location along the optical axis 2 through the lens barrel 10. In a representative example, a maximum outside diameter of the lens barrel 10 is about 4.75 mm and an inside diameter is about 3.6 mm, The outside diameter can be stepped so that portions of the lens barrel have outside diameters of 4.7 mm and 4.6 mm as well.

As shown in FIG. 1, an annular O-ring or gasket 20, a first lens element 30, a first aperture plate 40, a second lens element 50, an aperture stop 60, a spacer element 70, a third lens element 80, a second aperture plate 90, and a fourth lens element 100 are situated object-wise to image-wise along the axis 2. The gasket 20 has an outer diameter that allows it to be inserted inside the barrel 10 and an inner diameter selected so as to seal the first lens element against the lip 15 of the distal rim 14 so as to prevent air from entering the optical assembly 5. In one example, the O-ring 20 is made of a polymer such as an ethylene propylene co-polymer, a fluorocarbon such as vinylidene fluoride-hexafluoropropylene, acrylonitrile-butadiene copolymers, or other compliant materials.

The first lens element 30 has a negative power and is situated image-wise of the gasket 20. The aperture plate 40 comprises an annular ring made of, for example, a black polyester material such as, for example, polyethylene terephthalate or the like that is situated image-wise of the first lens 30. The aperture plate 40 defines an aperture 41 and has an outer diameter configured so that the aperture plate 40 fits within the lens barrel 10, while a diameter of the aperture 41 is selected to reduce flare in the optical assembly.

A second lens 50 having a positive refractive power is situated image-wise of the aperture plate 40 along the axis 2. An aperture stop plate 60 is situated image-wise of the second lens 50 and defines an aperture 61 that serves as an aperture stop for the optical assembly 5. The aperture stop plate 60 is typically an annular disk of a black polyester material or the like having an outer diameter selected so as to fit within the lens barrel 10. A diameter of the aperture 61 is selected to provide a desired f-number or numerical aperture for the optical assembly 5.

A spacer element 70 is situated image-wise of the aperture stop 60 and can be made of, for example, black plastic material or the like. A third lens 80 has a positive refractive power and is situated image-wise of the spacer 70. A second aperture plate 90 is situated image-wise of the third lens 80 and defines an aperture 91 and can be made of, for example, a black polyester material or the like. A fourth lens 100 having a negative refractive power is situated image-wise of the second aperture plate 90 along the axis 2.

Additional details of representative individual elements of the optical assembly 5 are shown in FIGS. 2-11 and described further below. Unless otherwise noted, all dimensions referred to in either this description or the accompanying drawings are in millimeters. In some examples, lens elements can be conveniently manufactured by injection molding. For such elements, both optical surface portions and mechanical mounting portions can be provided in a common part. In the description below, portions intended as refractive lens surfaces are referred to as optical surface portions.

FIGS. 2A-2B illustrate further details of the lens barrel 10. As shown in FIGS. 2A-2B, the lens barrel 10 is a tubular, hollow barrel having a proximal rim 12 and a distal rim 14. The distal rim 14 has an inner diameter that is less than the inner diameter of the lens barrel 10 so that the distal rim 14 forms a lip 15 to secure optical elements within the lens barrel 10. In one example, the proximal rim 12 includes one or more slots or notches 16 to form tabs 22, 24 that can be heated or otherwise formed to bend over the proximal-most optical element in the optical assembly 5, i.e., the lens 100 in the example of FIG. 1. In this way, the lens assembly can be secured by thermal welding or with an adhesive. With the proximal rim secured over the lens 100, the lenses, spacers, aperture plates, and the aperture stop plate are retained within the lens barrel 10. In one example, the lens barrel 10 is made of an acrylic or other plastic such as, for example, C1200-HF100 plastic or other plastics, metals, ceramics, or other materials. In typical applications, the distal rim 14 is object-wise of the proximal rim 12 along the optical axis 2.

Figure 3B:
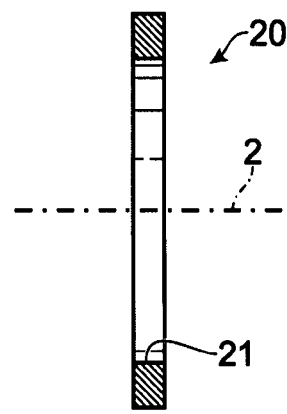

FIGS. 3A-3B illustrate further details of the gasket 20 that is configured to be situated within the lens barrel 10 at the distal rim 14 to form a seal between the distal rim 14 of the lens barrel 10 and the first lens element 30. The gasket 20 is formed of an elastomeric material that is somewhat compressible in order to allow the gasket 20 to provide a substantially airtight seal between the distal rim 14 of the barrel 10 and the first lens element 30. Typically, the tabs 22, 24 of the lens barrel 10 are configured to urge the lenses and other elements of the lens assembly towards the gasket 20 so that the gasket 20 presses against the distal rim 14 so as to form a seal. An aperture 21 of the gasket 20 is selected to avoid hindering light transmission through the optical assembly. In a typical example, an outer diameter of the gasket 20 is about 3.7 mm, an inner diameter is about 2.9 mm, and an uncompressed gasket thickness is about 0.3 mm. In some examples, the uncompressed gasket has a rectangular, square, or circular cross-section.

Figure 4A:
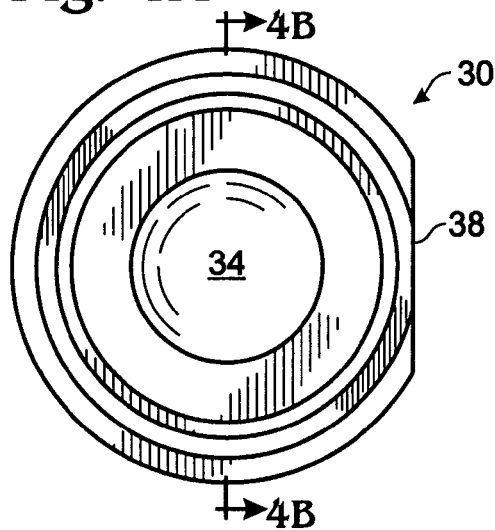
FIGS. 4A-4B illustrate a first lens of the representative optical assembly of FIG. 1.
Figure 4B:
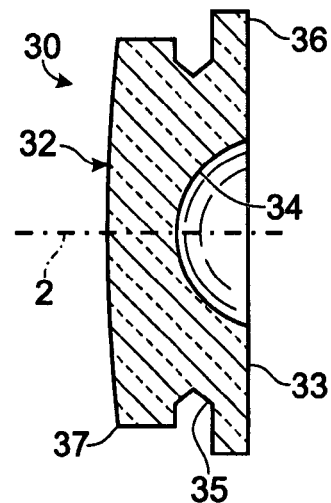

FIGS. 4A-4B illustrate a representative example of the first lens element 30 that defines optical lens surfaces as well as convenient mounting or other mechanical features. In this example, the first lens 30 has an object-side surface 32 that is substantially spherical and convex having a radius of curvature R=+60 mm. An image side surface 33 of the first lens 30 includes a concave, aspheric lens surface portion 34 having a diameter of about 1.58 mm. (Surface constants for this and other surfaces are listed below in Table 2.) A center thickness of the first lens 30 (between the surface 32 and the lens portion 34 ) is about 0.778 mm.

A V-shaped channel 35 of axial thickness of about 0.3 mm and inner diameter of about 2.6 mm extends around the outer circumference of the lens element 30. The gasket 20 is configured to be situated at least partially in the channel 35 so as to seal the lens assembly. A rim 36 is situated image-wise of the channel 35 and has a diameter of about 3.6 mm and an axial thickness of about 0.3 mm and a corresponding object-wise rim 37 has a diameter of about 3.2 mm. The image side rim 36 is configured so serve as a spacer between the first lens 30 and an adjacent optical element. For injection-molded parts, a circumferential portion 38 of the first lens 30 is typically flat to allow space for any gate vestige that is a by-product of the injection molding process such that the lens can fit into the lens barrel 10.

Figure 5A:
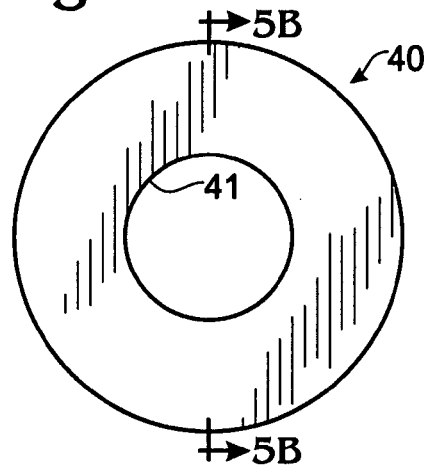
FIGS. 5A-5B illustrate a first flare-reducing aperture plate of the representative optical assembly of FIG. 1.
Figure 5B:
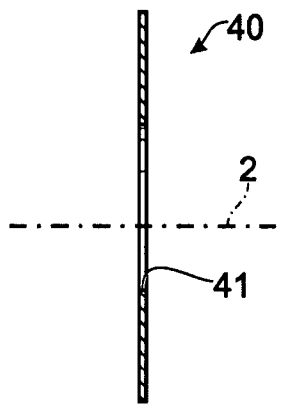

The first aperture plate 40 is illustrated in FIGS. 5A-5B. The first aperture plate can be formed of a black polyester or other plastic material or the like and defines an aperture 41 selected to reduce flare. Typically, the aperture plate 40 has an outside diameter of about 3.55 mm and has an axial thickness of about 0.05 mm, and the aperture 41 is substantially circular and has a diameter of about 1.53 mm.

Figure 6A:
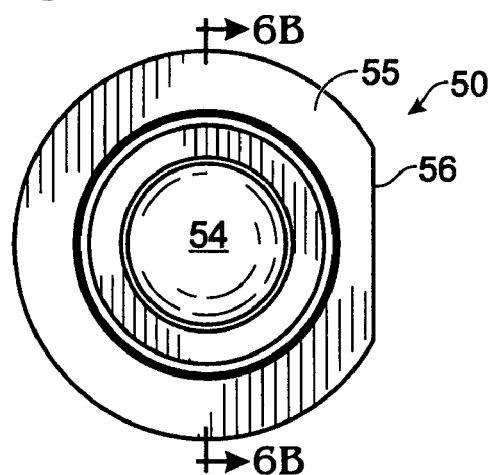
FIGS. 6A-6B illustrate a second lens of the representative optical assembly of FIG. 1.
Figure 6B:
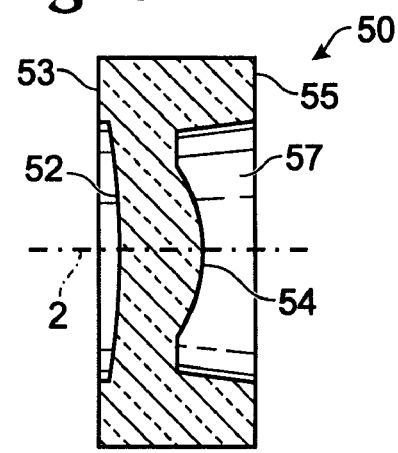

A representative example of the second lens element 50 is illustrated in FIGS. 6A-6B. The second lens element 50 has an axial thickness of about 0.8 mm and an outside diameter of about 3.60 mm, and includes an object side optical surface 52 that is concave and has a radius of curvature of about 8.125 mm. An image side optical surface portion 54 is a convex aspheric surface situated within a tapered aperture 57 having a minimum inside diameter of about 2.2 mm. An object-wise rim 53 has an axial thickness of about 0.138 mm measured from a most object-wise surface of the first lens element 50 to a most-image-wise portion of the optical surface 52. An image-wise rim 55 has an axial thickness of about 0.54 mm measured between a most image-wise surface of the second lens 50 and a most image-wise portion of the optical surface 54. As shown in FIG. 6B, a circumferential portion 56 of the second lens element 50 is flattened to allow space for any gate vestige in injection molding.

Figure 7A:
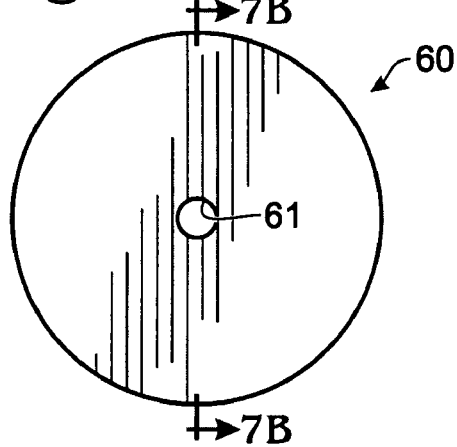
FIGS. 7A-7B illustrate an aperture stop of the representative optical assembly of FIG. 1.
Figure 7B:
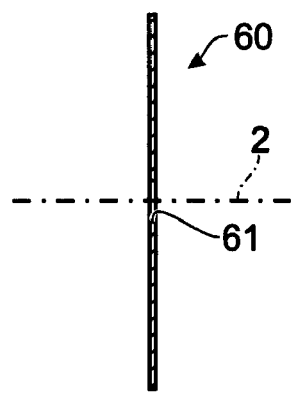

Referring to FIGS. 7A-7B, the aperture stop 60 is formed as a circular disk about 3.55 mm in diameter and having an axial thickness of about 0.05 mm, and includes a central aperture 61 having a diameter of about 0.38 mm. The aperture stop 60 is conveniently formed of a black plastic material such as, for example, a black polyester material such as polyethylene terephthalate. The diameter of the central aperture can be selected based on an intended lens f-number, and in the illustrated embodiment, the central aperture diameter provides an f-number of about 7.2.

Figure 8A:
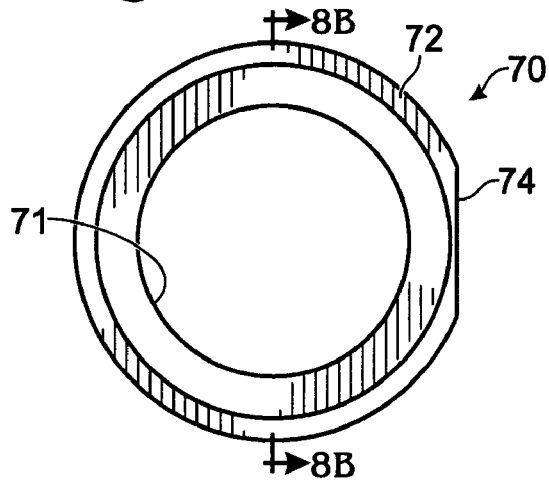
FIGS. 8A-8B illustrate a spacer of the representative optical assembly of FIG. 1.
Figure 8B:
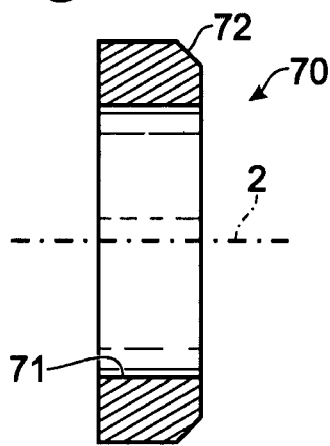

As shown in FIGS. 8A-8B, the spacer 70 has an axial thickness of about 0.89 mm and defines an aperture 71 having a diameter of about 2.4 mm. The spacer 70 has a flattened circumferential portion 74 for any gate vestige so that it does not protrude beyond the spacer outer diameter of about 3.52 mm. The spacer 70 can be formed of a black plastic such as acrylic or other plastic such as, for example, C1200 HF-100 plastic material. Other plastics, metals, glasses, or ceramic materials can be used. An outer diameter of the spacer 70 includes a 45 degree chamfered portion 72.

Figure 9A:
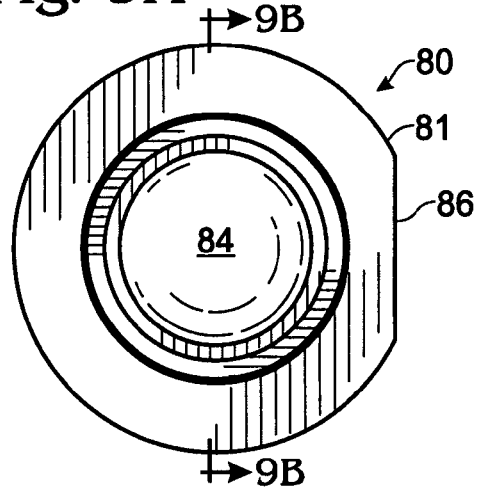
FIGS. 9A-9B illustrate a third lens of the representative optical assembly of FIG. 1.
Figure 9B:
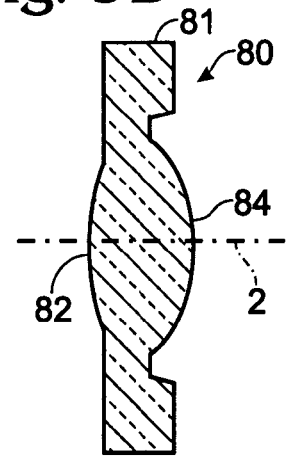

As shown in FIGS. 9A-9B, the third lens element 80 has an object side optical surface portion 82 and an image side optical surface portion 84. The object side surface portion 82 is convex and spherical, and has a radius of curvature of about 2.831 mm and a diameter of about 1.7 mm. The image side surface portion 84 is a convex asphere of diameter of about 1.96 mm. The third lens element 80 includes a circumferential mounting portion 81 from which the object-side optical surface portion 82 extends axially object-wise about 0.131 mm and from which the image-side optical surface portion 84 extends axially image-wise about 0.14 mm. A center thickness is about 0.9 mm. The third lens element 80 includes a flattened surface 86 at its circumference to facilitate injection molding.

In representative examples, the lens elements 30, 50, 80 can be made of ZeonexB E48R plastic material from Zeon, Inc., a cyclo-olefin polymer, or other suitable lens plastics to allow the lenses to be injection molded. Some such optical plastics have indices of refractive $n_d$ of about 1.5251, 1.5311, or 1.5094 at a wavelength of 587.6 nm, and Abbe numbers of about 56. The injection molded lens elements are typically anti-reflection coated. While plastic lenses are convenient, optical glasses, fused silica, or other materials can be used for the lens elements 30, 50, 80. Typical materials have similar indices of refraction and Abbe numbers.

Figure 10A:
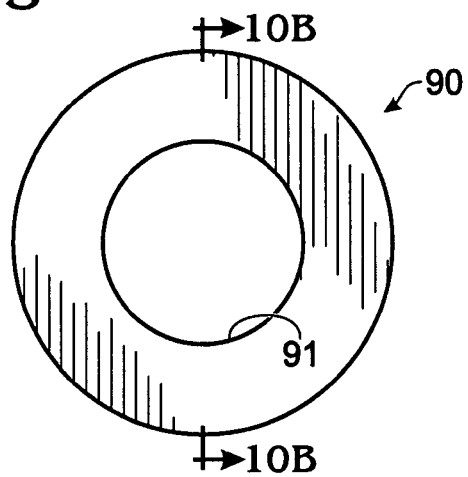
FIGS. 10A-10B illustrate a second flare-reducing aperture plate of the representative optical assembly of FIG. 1.
Figure 10B:
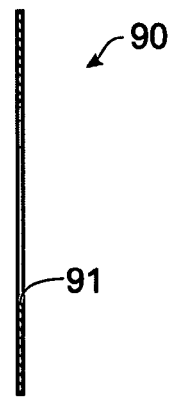

As shown in FIGS. 10A-10B, the second aperture plate 90 defines a circular aperture 91 having a diameter of about 1.88 mm that is selected for flare reduction. The aperture plate 90 is preferably made of a black polyester material such as, for example, polyethylene terephthalate or the like, and is about 0.05 mm thick.

Figure 11A:
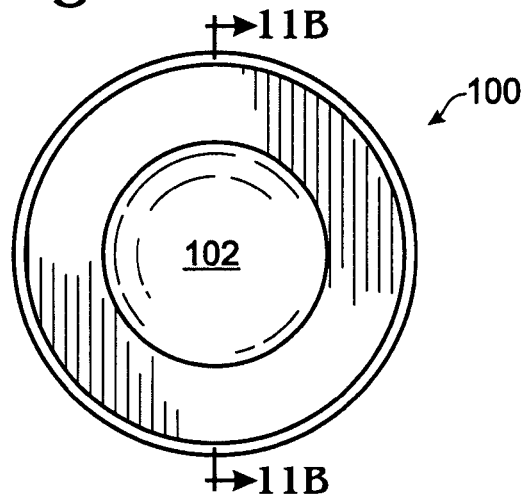
FIGS. 11A-11B illustrate a fourth lens of the representative optical assembly of FIG. 1.
Figure 11B:
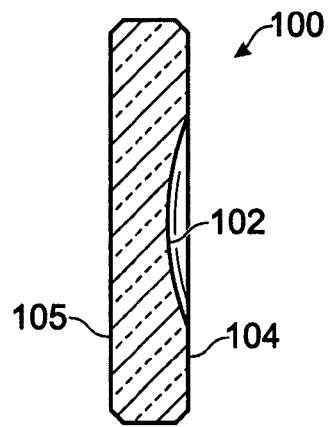

The fourth lens element 100 is illustrated in FIGS. 11A-11B. The fourth lens element is typically made of a relatively dispersive "flint" type glass so as to provide chromatic aberration correction. In typical examples, ZF-52 optical glass that is available from CDGM Glass Company Ltd is used. The lens element 100 includes an object side optical surface 102 having a diameter of about 2.0 mm and an image side surface 105. A diameter of the fourth lens element is about 3.6 mm. The object side optical surface 102 is concave with a radius of curvature of about 2.674 mm and extends axially image-wise from a peripheral object-wise flat portion 104 about 0.194 mm. The image side surface 105 is a flat (plano) surface. The fourth lens 100 has a center thickness of about 0.5 mm.

Complete lens specifications for a representative multi-element lens are listed in Tables 1-3. Table 1 contains basic lens data such a focal length, f-number, field of view, distortion, image field diameter, and entrance pupil diameter. Table 2 contains surface curvatures and lens materials. Surfaces 1, 2 are the object-wise and image-wise optical surfaces of the first lens, respectively, surfaces 3, 4 are the object-wise and image-wise optical surfaces of the second lens, surfaces 6, 7 are the object-wise and image-wise optical surfaces of the third lens, and surfaces 8, 9 are the object-wise and image-wise optical surfaces of the fourth lens. Surface 5 is the aperture stop. The radius of curvature of plano surfaces is noted as infinite ("inf") in Table 2. As discussed above, some surfaces are aspheric, and aspheric surfaces are noted with a * in Table 2. Aspheric constants for these surfaces are listed in Table 3. Exit pupil distance is 2.02 mm nominal from the last lens surface (i.e., the most image-wise surface of the fourth lens element 100). A distance from the distal rim 14 of the lens barrel 10 to an image plane is 7.63 mm with a 0.5 mm glass window at an image sensor, such as a CMOS imager, with a 7 mm object distance.

In the example of Table 2, XEON E48R optical plastic is used for three lens elements (30, 50, 80) and ZF-52 glass available from CDGM Glass Company Ltd. is used for one lens element (100). Materials from other vendors can also be used. For convenience, design refractive indices and Abbe numbers are included in Table 2.

Because this lens assembly is intended for use in forming an image of an object on an image sensor array, a typical window for such an array is include in Table 1 in conjunction with surfaces 10, 11 associated with a 0.5 mm thick window of CDGM Glass Company Ltd K-9 optical glass.

TABLE 1

Basic Lens Specifications

| Focal length | 1.8 mm |
|---|---|
| F# | 7.2 |
| Field of View (FOV) | 140 degrees |
| Distortion | within 15% of f-theta at maximum FOV |
| Image Field Diameter | 4.30 mm |
| Entrance Pupil Diameter | 0.22 mm |
| Object Distance | 10 mm |
| Back Focal Distance | 2.8 mm |
| Total Track | 7.76 mm |
| Magnification | 0.17 |
| On-Axis Polychromatic Contrast Transfer Function | >80% at 30 lp/mm (negative target) at object distance of 7 mm from first lens vertex |

TABLE 2

Lens Surface Specifications. (Surfaces noted with * are aspheric.)

| Surf. No. | Radius of Curvature | Thickness | Material | Refractive Index | Abbe Number |
|---|---|---|---|---|---|
| OBJECT | inf | 7.000 | | | |
| 1 (32) | +60.000 | 0.500 | E48R | 1.531 | 56.04 |
| 2* (34) | +0.973 | 0.782 | | | |
| 3 (52) | −8.125 | 0.800 | E48R | 1.531 | 56.04 |
| 4* (54) | −1.491 | 0.538 | | | |
| 5. STOP | | 0.804 | | | |
| 6 (82) | +2.831 | 0.900 | E48R | 1.531 | 56.04 |
| 7* (84) | −1.193 | 0.100 | | | |
| 8 (92) | −2.674 | 0.500 | ZF52 | 1.847 | 23.8 |
| 9 (94) | inf | 2.200 | | | |
| 10 | inf | 0.500 | K9 | 1.516 | 64.1 |
| 11 | inf | 0.138 | | | |
| IMAGE | | | | | |

TABLE 3

Aspheric Surface Specifications

| Surf. | K | $a_2$ | $a_3$ | $a_4$ |
|---|---|---|---|---|
| 2* | +0.5073543 | +0.0 | +0.0 | +0.0 |
| 4* | +0.0 | −0.018796213 | −0.036606083 | −0.068263035 |
| 7* | +0.0 | +0.11189657 | +0.014471055 | +0.044036317 |

Figure 13:
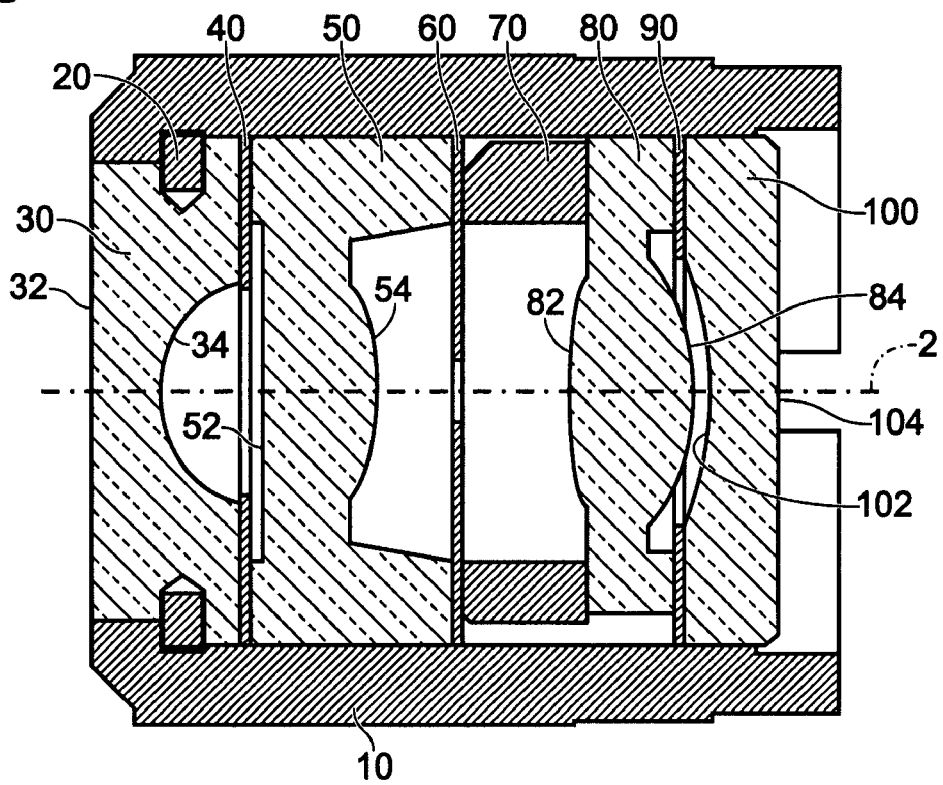
FIG. 13 is a sectional view of the optical assembly of FIG. 1.

FIG. 13 is a sectional view of a completed lens assembly such as illustrated in FIG. 1. Some elements (70, 80) are not necessarily symmetric about the optical axis 2 as assembled in order to, for example, provide relief space to retain excess adhesive for assembly. The elements are typically assembled in the lens barrel in a clean room environment. While the object is noted as planar in Table 2, a lens assembly can be configured for imaging of a curved object having, for example, a radius of curvature of 10 mm, 20 mm, or other radius.

Figure 12:
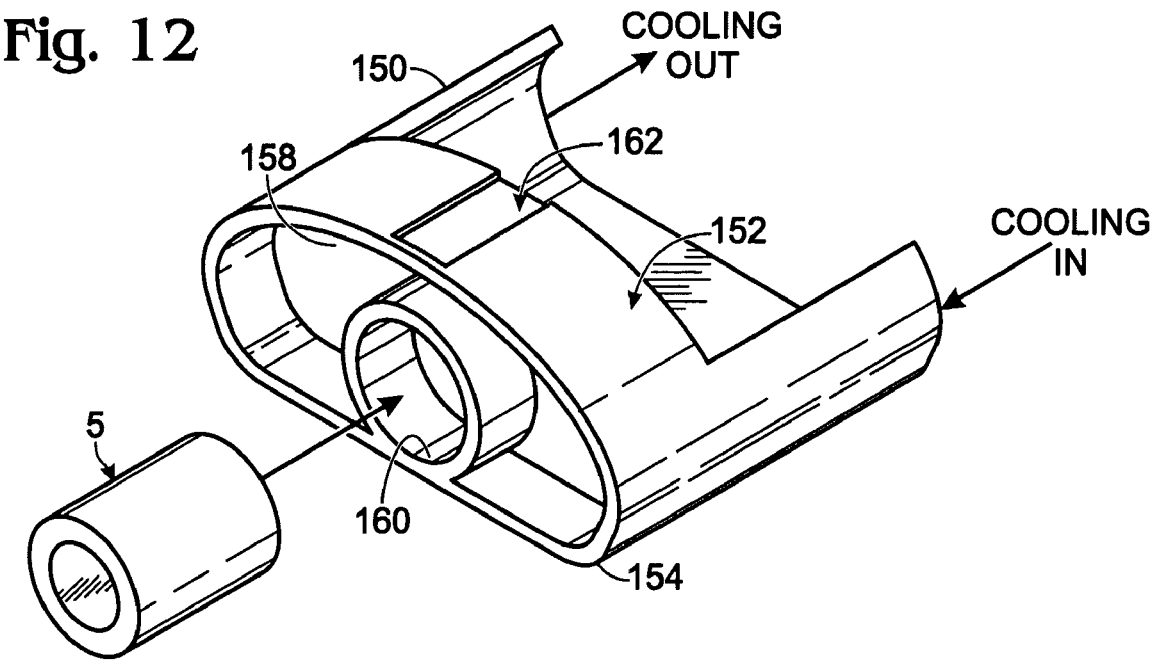
FIG. 12 illustrates a representative image sensor insert configured to situate the representative optical assembly of FIG. 1 so as to direct an image of an object to an image sensor.

FIG. 12 illustrates one suitable environment where optical assemblies as disclosed herein can be used. An image sensor insert 150 comprises a generally semicircular component with a rounded upper portion 152 and a generally flat bottom surface 154. The image sensor insert 150 is designed to be slidably received within a cap of an imaging endoscope or other medical device. Further details of the image sensor insert and cap of the imaging endoscope are set forth in U.S. patent application Ser. No. 11/407,700, filed Apr. 20, 2006, which is herein incorporated by reference. The image sensor insert 150 includes a cooling channel 158 through which a cooling liquid or gas can flow. A thermally clad circuit board (not shown), including one or more illumination LEDs, can be situated in the cooling channel 158 in order to transfer heat from the illumination LEDs to the cooling liquid or gas. A circular bore 160 can be provided at the center of the image sensor insert 150 or other location and is configured to receive an optical assembly such as the optical assembly 5. In a representative example, the bore 160 is provided with a stop that aids in focusing the optical elements in the optical assembly 5 onto an image sensor positioned on a surface 162 that is behind and aligned with the circular bore 160. Further details of image sensor inserts and caps of imaging endoscopes are set forth in U.S. patent application Ser. No. 11/407,700 as noted above.

As discussed above, the optical assembly 5 can be assembled by positioning each of the individual optical elements in the lens barrel 10 in the appropriate order. The proximal-most element (the lens 100) is then urged toward the distal end 14 of the lens barrel by the lens barrel tabs. The various lenses, spacers, and aperture plates are thus secured in the lens barrel 10 and compress the gasket 20 so that an airtight seal is formed between the distal or object side of the optical assembly 5 and the first lens element 30. Imaging components of an endoscope or other medical device are arranged by positioning an image sensor behind the bore 160 in the image sensor insert 150. The optical assembly 5 is inserted into the bore 160 and fixed with an adhesive or fastener. The illumination LEDs can be mounted on a circuit board that is placed into the cooling channel 158.

While illustrative embodiments have been illustrated and described, it will be appreciated that various changes can be made therein without departing from the scope of the disclosure. For example, the lens barrel can be formed by the bore 160 in the image sensor insert. The optical elements can be stacked and compressed within the bore in order to seal the assembly. While representative examples have particular focal lengths, f-numbers, lens barrel outside diameters, total track lengths and other dimensional parameters, in other examples these parameters can be selected for a particular application. For example, a smaller outside diameter can be provided (perhaps with a reduced focal length, increased f-number, or a decreased lens barrel thickness or combination thereof) so as to permit a larger working channel for surgical and other instruments to be used based on images provided by a lens assembly/image sensor combination. Alternatively, larger diameters, longer focal lengths, reduced f-numbers, or other increased dimensional parameters can be selected. Further embodiments of the invention may be duplicative of or in addition to those described above. We claim all that is encompassed by the appended claims.

We claim:

1. A multi-element lens, comprising a plurality of lens elements situated so that an effective focal length is about 1.8 mm, an f-number is less than about 8, and distortion is within about 15% off-theta at full field of view of 140 degrees, wherein the plurality of lens elements includes, from object-wise to image-wise along an optical axis, a first lens element, a second lens element, and a third lens element of a common optical material, and a fourth lens element of a different lens material.

2. The multi-element lens of claim 1, wherein the first, second, and third lens elements are made of a common optical plastic, and the fourth lens element is made of a flint glass, and the first through fourth lens elements have optical surfaces defined by, from a most object-wise surface to a most image-wise surface:

| Surface | Radius of Curvature |
|---------|---------------------|
| 1 | +60.000 |
| 2 | +0.973 |
| 3 | −8.125 |
| 4 | −1.491 |
| 5 | +2.831 |
| 6 | −1.193 |
| 7 | −2.674 |
| 8 | inf. |

3. The multi-element lens of claim 1, wherein the first, second, and third lens elements are made of a common optical plastic, and the fourth lens element is made of a flint glass, the optical plastic has an Abbe number of about 24 and the flint glass has an Abbe number of about 56.

4. The multi-element lens of claim 1, wherein most image-wise surfaces of the first lens element, the second lens element, and the third lens element are aspheric surfaces.

5. The multi-element lens of claim 1, wherein most image-wise surfaces of the first lens element, the second lens element, and the third lens element are aspheric surfaces, the aspheric surfaces of the first lens element, the second lens element, and the third lens element are defined by

| K | $a_2$ | $a_3$ | $a_4$ |
|---|-------|-------|-------|
| +0.5073543 | 0.0 | 0.0 | 0.0 |
| +0.0 | −0.018796213 | −0.036606083 | −0.068263035 |
| +0.0 | +0.11189657 | +0.014471055 | +0.044036317 | wherein K is a conic constant, and $a_2$, $a_3$, and $a_4$ are aspheric power series coefficients.

6. The multi-element lens of claim 1, further comprising a first aperture plate defining a flare reducing aperture situated between the first lens element and the second lens element and a second aperture plate situated between the third lens element and the fourth lens element.

7. The multi-element lens of claim 1, further comprising a lens barrel configured to receive the first, second, third, and fourth lens elements, wherein the first lens element includes a circumferential channel and a rim adjacent the channel so that a compliant gasket retained in the circumferential channel is situated to be compressed between the rim and a lip of the lens barrel.

\* \* \* \* \*

UNITED STATES PATENT AND TRADEMARK OFFICE
CERTIFICATE OF CORRECTION

PATENT NO. : 7,933,079 B2
APPLICATION NO. : 11/801332
DATED : April 26, 2011
INVENTOR(S) : Ning et al.

Page 1 of 1

It is certified that error appears in the above-identified patent and that said Letters Patent is hereby corrected as shown below:

Claim 1, col. 11, line 31, "15% off-theta" should read --15% of f-theta--.

Signed and Sealed this
Twenty-first Day of June, 2011

David J. Kappos
*Director of the United States Patent and Trademark Office*